(12) United States Patent
Fritzinger (10) Patent No.: US 8,572,860 B2
(45) Date of Patent: Nov. 5, 2013

(54) DOUBLE-ENDED DEPTH GAGE

(75) Inventor: Daniel Fritzinger, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 198 days.

(21) Appl. No.: 13/274,534

(22) Filed: Oct. 17, 2011

(65) Prior Publication Data

US 2013/0096565 A1    Apr. 18, 2013

(51) Int. Cl.
*A61B 5/103* (2006.01)
*G01B 5/18* (2006.01)

(52) U.S. Cl.
USPC ............... 33/512; 33/836; 600/587; 606/102

(58) Field of Classification Search
USPC ...................... 33/512, 536; 600/587; 606/102
See application file for complete search history.

(56) References Cited

U.S. PATENT DOCUMENTS

| | | | |
|---|---|---|---|
| 4,710,075 A * | 12/1987 | Davison | 33/512 |
| 5,186,180 A * | 2/1993 | Bellas | 33/512 |
| 6,450,976 B2 * | 9/2002 | Korotko et al. | 600/587 |
| 7,165,336 B2 | 1/2007 | Kim | |
| 7,444,756 B2 * | 11/2008 | Kim | 33/512 |
| 7,607,238 B2 * | 10/2009 | Kim et al. | 33/836 |
| 7,676,943 B2 | 3/2010 | Kim et al. | |
| 2009/0157088 A1 | 6/2009 | Mengato | |
| 2010/0137874 A1 * | 6/2010 | Kim et al. | 606/102 |
| 2013/0072942 A1 * | 3/2013 | LeBeau et al. | 606/102 |
| 2013/0110120 A1 * | 5/2013 | Baroud et al. | 606/102 |

* cited by examiner

*Primary Examiner* — G. Bradley Bennett
(74) *Attorney, Agent, or Firm* — Harness, Dickey (57) ABSTRACT

An instrument for measuring a depth of a hole in bone can comprise an instrument body having a cannulated sleeve that extends between a first end and a second end. A first reference portion can be disposed at the first end and a second reference portion can be disposed at the second end. A probe can selectively and alternatively translate in first and second opposite directions through the cannulated sleeve between a first measuring position and a second measuring position. The probe extends outwardly a distance spaced from the first reference portion in the first measuring position and extends outwardly a distance spaced from the second reference portion in the second measuring position.

20 Claims, 6 Drawing Sheets

FIG-9

DOUBLE-ENDED DEPTH GAGE

FIELD

The present disclosure relates generally to instruments used to determine a depth of a bone hole and, more particularly, to a double-ended depth gage that has a first end configured to register relative to a first aperture in a bone plate and a second end configured to register relative to a second aperture in the bone plate where the first and second apertures are of distinctly different diameters.

BACKGROUND

This section provides background information related to the present disclosure which is not necessarily prior art.

In some instances, it may be desirable to fix a fractured bone with a bone plate. In many examples, bone plates are configured with threaded apertures having different diameters that may be used to accept bone screws having different diameters and/or lengths. As can be appreciated, it is desirable to incorporate a bone screw having the correct length such that a distal tip of the bone screw does not extend beyond the far side of the bone. Similarly, implanting a bone screw that has a length that is too short can reduce the effective purchase of the bone screw, which is also undesirable.

In this regard, optimization of the length of a bone screw can be critical for achieving proper fixation of a bone plate. A depth gage can be used to measure the depth of a prepared bone hole to determine the appropriate size bone screw. Often, each size of bone screw requires a specific depth gage. In this regard, a surgeon may be required to utilize different depth gages for measuring the depth of a prepared bone hole relative to a given threaded aperture of the bone plate. It is desirable to quickly and efficiently measure the depth of a hole prepared in bone that may be configured to receive a bone screw having a first diameter as well as another hole prepared in the bone that may be configured to receive a bone screw having a second distinct diameter.

SUMMARY

This section provides a general summary of the disclosure, and is not a comprehensive disclosure of its full scope or all of its features.

An instrument for measuring a depth of a hole in bone can comprise an instrument body having a cannulated sleeve that extends between a first end and a second end. A first reference portion can be disposed at the first end and a second reference portion can be disposed at the second end. A probe can selectively and alternatively translate in first and second opposite directions through the cannulated sleeve between a first measuring position and a second measuring position. The probe extends outwardly a distance spaced from the first reference portion in the first measuring position and extends outwardly a distance spaced from the second reference portion in the second measuring position.

According to additional features, the instrument can further comprise an actuator that is coupled to the probe and configured to slidably advance along the instrument body causing the probe to selectively and alternatively deploy and retract from the respective first and second ends of the instrument body. The probe can include first and second hooked ends formed at opposite ends thereof. The first reference portion can comprise a first distal tip having a first elongated body that connects the first registering surface and a first conical connection portion. The second reference portion can comprise a second distal tip having a second elongated body that connects the second registering surface and a second conical connecting portion.

According to still other features, the first elongated body can have a first outer diameter. The second elongated body can have a second diameter. The first and second diameters can be distinct. The cannulated sleeve can define an elongated slot formed therethrough. The actuator can be configured to slidably translate along the elongated slot. The actuator can have a reference line formed thereon. The instrument body can have gradations formed thereon. The reference line can be configured to operably align with the gradations formed on the instrument body.

A method for measuring a depth of a hole in a bone can include positioning a bone plate against the bone. A hole can be prepared through the bone from a first surface to a second surface. A size of threaded aperture defined through the bone plate can be determined. One of a first or second end of an instrument can be positioned relative to the threaded aperture based on the determination. The first end can have a first registering surface while the second end can have a second registering surface. The first and second registering surfaces can have distinct geometries for alternatively registering with different sized threaded apertures of the bone plate. A probe can be deployed with an actuator from the positioned end of the instrument through the threaded aperture to a position through the bone hole. A hook formed on the probe can be positively engaged to the bone at the second surface. Gradations on the instrument can be referenced with a position of the actuator to determine the depth of the hole.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

The following discussion will be directed toward measuring a depth of a hole prepared through a radius of a patient. It will be appreciated, however, that the instrument and related method described herein may be used to measure a depth of a bone hole in other bones. Additionally, the following discussion will be directed toward an instrument and related method that engages or registers with a surface that defines a threaded aperture in a bone plate. It will be appreciated, however, that the instrument and related method described herein does not specifically require the use of a bone plate. In this regard, the instrument and related method can be used without a bone plate by registering directly onto a bone surface to determine a depth of a bone hole. Moreover, the instrument described herein may be used with other implants such as, but not limited to, intramedullary nails. In addition, the instrument described herein will be specifically described as having a first end that is specifically configured to be registered for use with a 2.7 mm bone screw and a second end that is specifically configured to be registered for use with a 3.5 mm bone screw. It will be appreciated, however, that the opposite ends of the instrument may be configured differently for use with other dimensioned bone screws.

Figure 1:
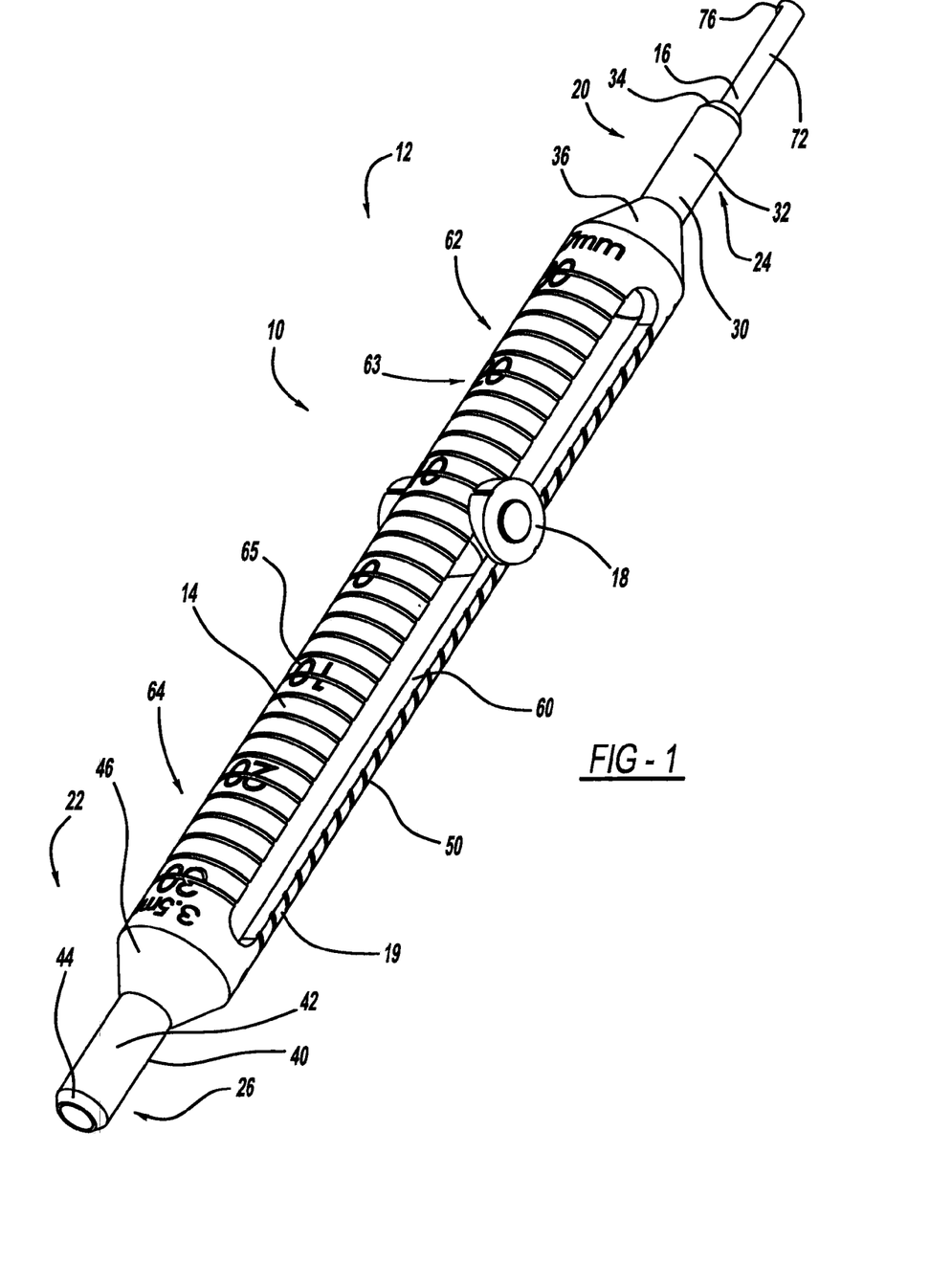
FIG. 1 is a front perspective view of an instrument in the form of a double-ended depth gage constructed in accordance to one example of the present teachings.
Figure 2:
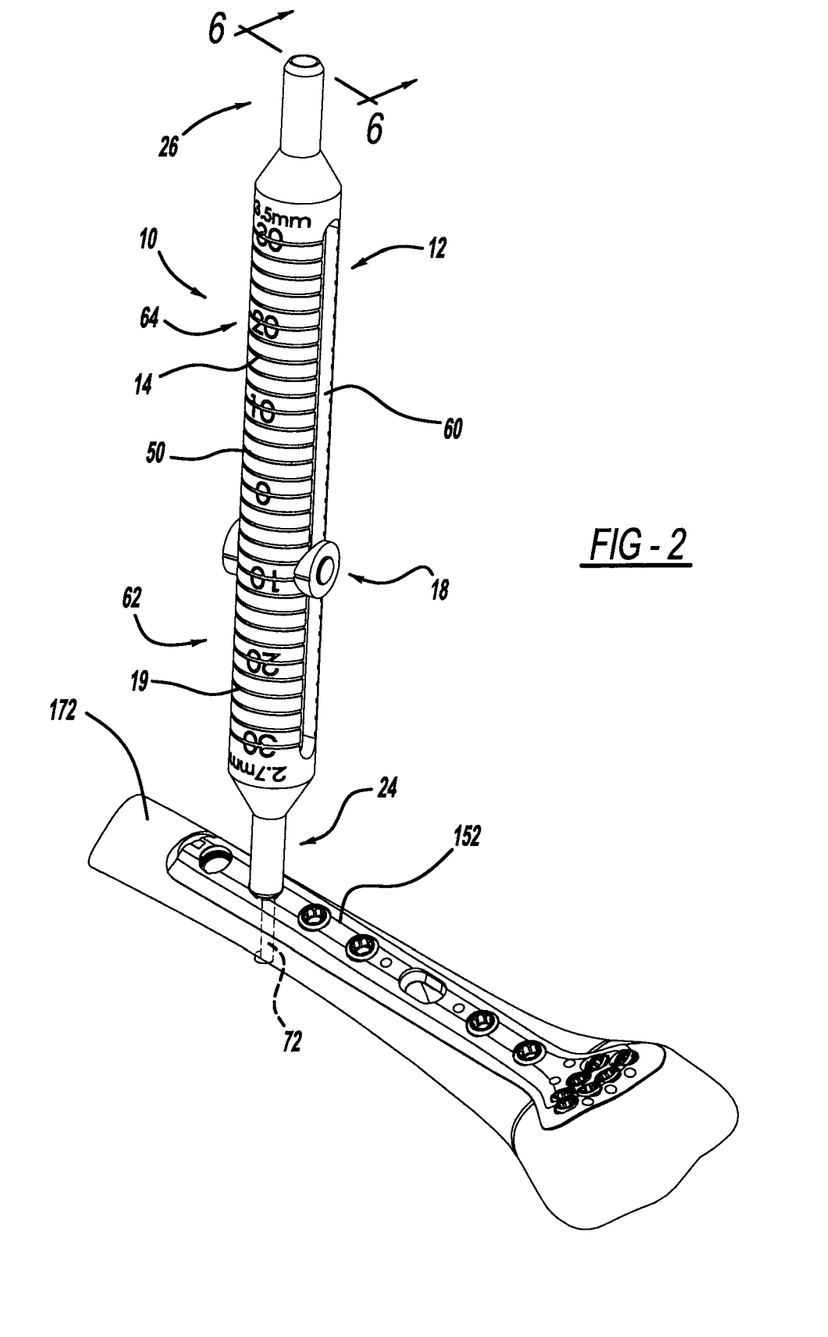
FIG. 2 is a front perspective view of an exemplary bone plate shown positioned relative to a radius and shown with the instrument of FIG. 1 measuring a depth of a hole prepared through the radius according to one example of the present teachings.
Figure 3:
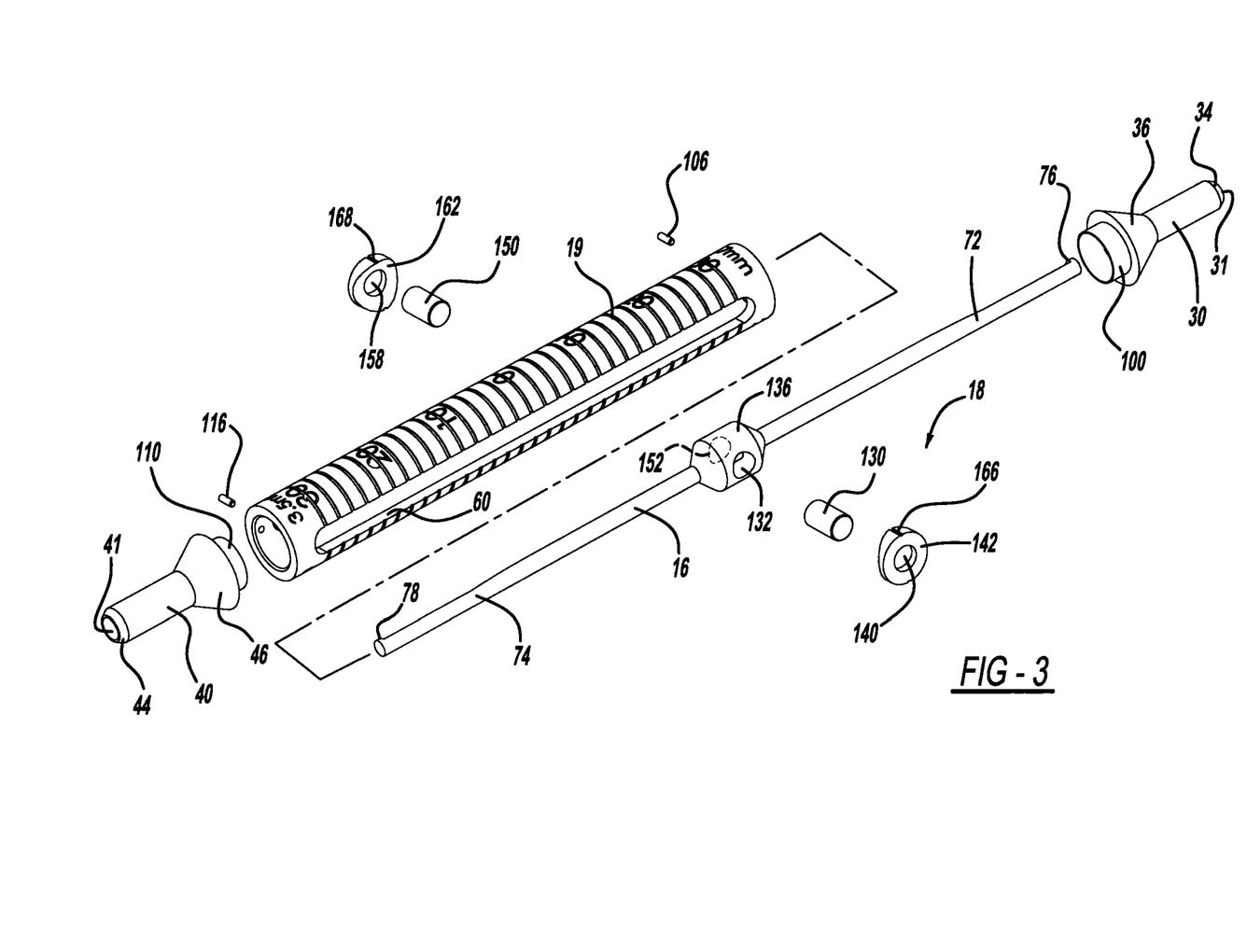
FIG. 3 is an exploded perspective view of the instrument of FIG. 1.
Figure 4:
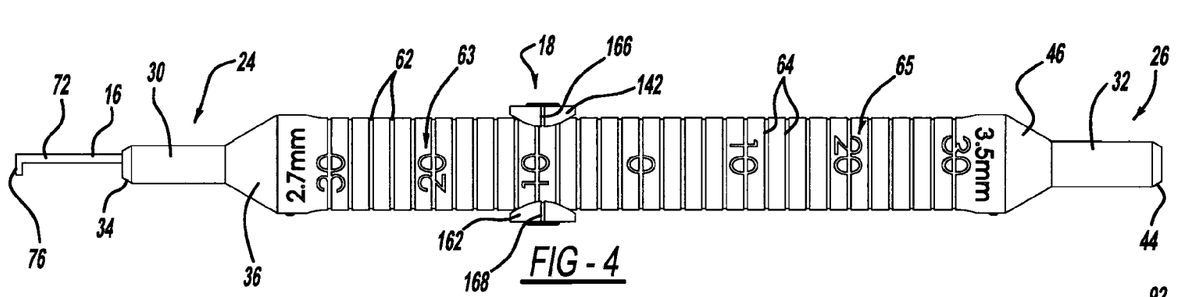
FIG. 4 is a side view of the instrument of FIG. 1.

With initial reference to FIGS. 1 and 2, an instrument constructed in accordance to one example of the present teachings is shown and generally identified at reference numeral 10. The instrument 10 is constructed in the form of a double-ended depth gage 12. The instrument 10 generally includes an instrument body 14, a probe 16 that slidably translates relative to the instrument body 16 and an actuator 18 coupled to the probe 16. The instrument body 14 can have a cannulated sleeve 19 that extends between a first end 20 and a second end 22. A first reference portion 24 can be disposed at the first end 20. A second reference portion 26 can be formed at the second end 22. The first reference portion 24 can generally comprise a first distal tip 30 having an opening 31 (FIG. 3). The first distal tip 30 can have an elongated body 32 that extends between a first registering surface 34 and a first conical transition portion 36. The second reference portion 26 can generally comprise a second distal tip 40 having an opening 41 (FIG. 3). The second distal tip 40 can have an elongated body 42 that generally extends between a second registering surface 44 and a second conical transition portion 46.

With continued reference to FIGS. 1 and 2 and additional reference to FIGS. 3-6, additional features of the instrument 10 will be described. The cannulated sleeve 19 generally includes a longitudinal body 50 that extends along a longitudinal axis 52 and defines an inner cavity 54 (FIG. 6). The cannulated sleeve 19 defines an elongated slot 60. A first series of gradations 62 and indicia 63 are formed on an outer surface of the cannulated sleeve 19. A second series of gradations 64 and indicia 65 are also formed on the outer surface of the cannulated sleeve 19. As will become appreciated, the first series of gradations 62 are generally associated with measurements taken from the first registering surface 34. Similarly, the second series of gradations 64 generally correspond to measurements taken from the second registering surface 44. In the particular example shown, the first reference portion 24 is configured to take depth measurements that correspond with the use of a first bone screw or a 2.7 mm bone screw. Likewise, the second reference portion 26 is specifically configured for taking measurements that correspond to use with a second bone screw or a 3.5 mm bone screw.

The probe 16 can include a first probe portion 72 and a second probe portion 74 (FIG. 3). The first probe portion 72 can be slidably advanced and retracted through the opening 31 of the first distal tip 30. Similarly, the second probe portion 74 can be slidably advanced and retracted through the opening 41 of second distal tip 40. In the example provided, the probe 16 is monolithically formed such that the first and second probe portions 72 and 74 are collectively formed thereon. The probe 16 can be formed of a rigid biocompatible material such as stainless steel. In other examples, the probe 16 can be formed of plastic and can be disposable. The probe 16 can still provide a degree of flexibility. The first probe portion 72 can include a first hook 76. The second probe portion 74 can include a second hook 78 formed thereon. As will be described more fully herein, the actuator 18 can be coupled to the probe 16 for slidably translating the probe 16 through the inner cavity 54 of the longitudinal body 50 to advance and retract the desired first or second probe portions 72 and 74.

Figure 5:
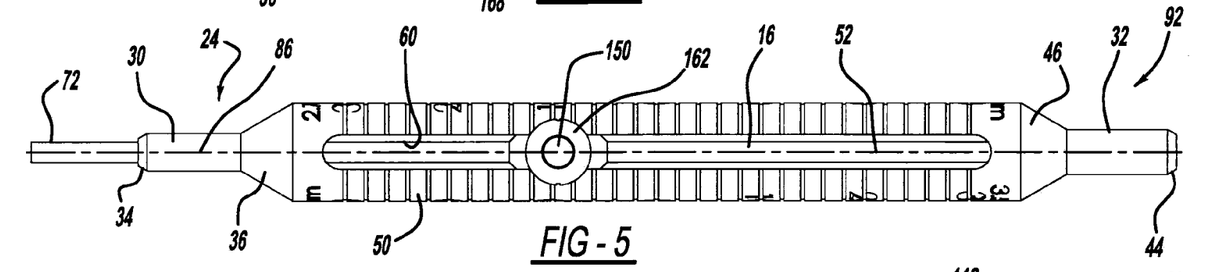
FIG. 5 is a side view of the instrument shown in FIG. 4 rotated ninety degrees along its longitudinal axis.
Figure 6:
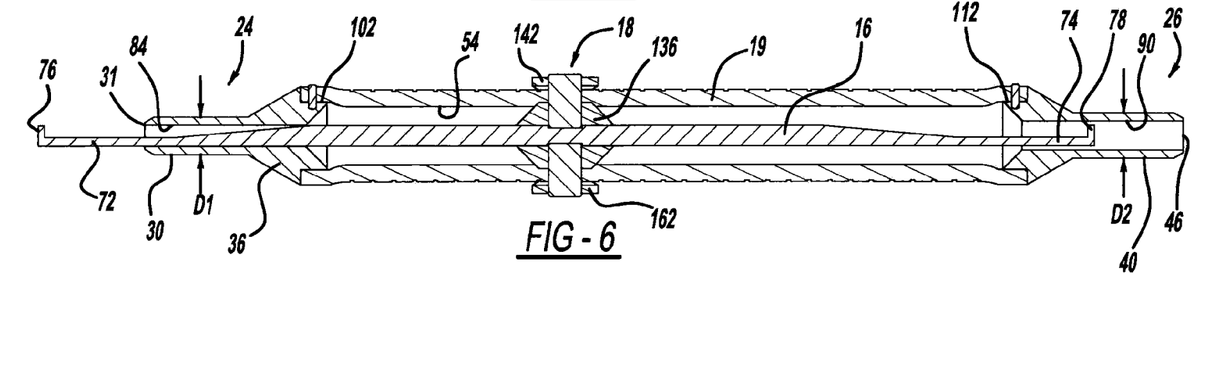
FIG. 6 is a cross-sectional view of the instrument taken along lines 6-6 of FIG. 2.

With particular reference now to FIGS. 5 and 6, additional features of the first and second distal tips 30 and 40 will be described. The first distal tip 30 generally defines a first cannulation 84 therethrough. The first distal tip 30 can have an outer diameter D1. The first cannulation 84 can be formed along a first axis 86 (FIG. 5). The second distal tip 40 can define a second cannulation 90 therethrough. The second cannulation 90 can be formed along a second axis 92.

The second distal tip 40 can have an outer diameter D2. The first diameter D1 and the second diameter D2 are distinct. In this regard, the first diameter D1 is configured to correspond to a bone screw having a first diameter (such as 2.7 mm). More particularly, as will be described herein, the diameter D1 is configured to allow for partial insertion of the first distal tip 30 into a correspondingly sized threaded aperture of a bone plate (FIG. 7) until the first registering surface 34 engages the threads formed on the threaded aperture. The second diameter D2 is configured to correspond to a bone screw having a second diameter (such as 3.5 mm). The second diameter D2 is configured to allow for partial insertion of the second distal tip 40 into a correspondingly sized threaded aperture of a bone plate until the second registering surface 44 engages the opposing threads of the threaded aperture. Because the first and second diameters D1 and D2 are distinct and specifically configured for use with a particularly sized bone screw (2.7 mm, 3.5 mm), a surgeon will know when the correct sized reference portion 24 or 26 has been used based on proper seating of the first or second registering surface 34 against the threads formed on the threaded aperture.

In one example, and as shown in FIG. 5, the first axis 86, the second axis 92, and the axis 52 of the cannulated sleeve 19 can all be coaxial. The first distal tip 30 can include an inset boss 100 that can be configured to nest within a first receiving end 102 formed on the cannulated sleeve 19. A pin 106 can fixedly connect the first distal tip 30 to the first receiving end 102 of the cannulated sleeve 19. The second distal tip 40 can include an inset boss 110 that can nest into a second receiving end 112 of the cannulated sleeve 19. Another pin 116 can connect the second distal tip 40 to the second receiving end 112 of the cannulated sleeve 19.

With particular reference now to FIGS. 3 and 6, additional features of the actuator 18 will be described. The actuator 18 can be coupled to the probe 16 and configured to slidably advance along the instrument body 14 causing the first and second probe portions 72 and 74 to selectively and alternatively deploy and retract from the openings 31 and 41 in the respective first and second reference portions 24 and 26. The actuator 18 generally includes a first shaft 130 having a first end that locates within a first opening 132 in a hub 136 connected to the probe 16. An opposite end of the shaft 130 can locate through a passage 140 formed through a button 142. The actuator 18 can additionally include a second shaft 150 that has a first end that locates into a corresponding opening 152 in the hub 136. An opposite end of the shaft 150 can locate through a passage 158 formed in a button 162. The actuator 18 is fixed with the hub 136 for concurrent movement with the probe 16.

As best illustrated in FIG. 6, the first and second shafts 130 and 150 can be configured to be generally coaxial to each other and transverse to the probe 16. The buttons 142 and 162 can include reference lines 166 and 168, respectively. The reference lines 166 and 168 can be used to visually identify the corresponding first or second series of gradations 62 and 64 when measuring a depth of a bone hole.

Figure 7:
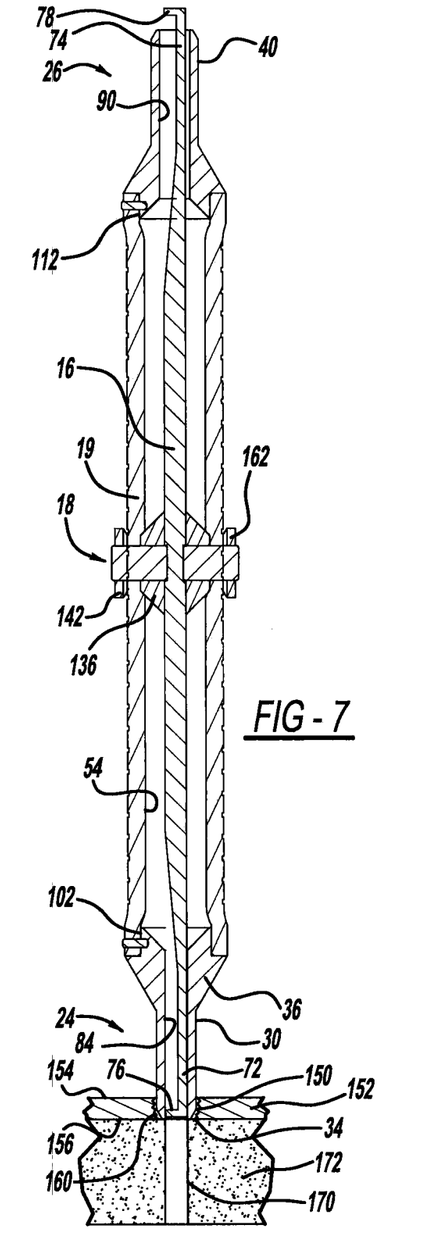
FIG. 7 is a cross-sectional view of the instrument of FIG. 1 and shown with a first end registering relative to a threaded aperture of the bone plate of FIG. 2.
Figure 8:
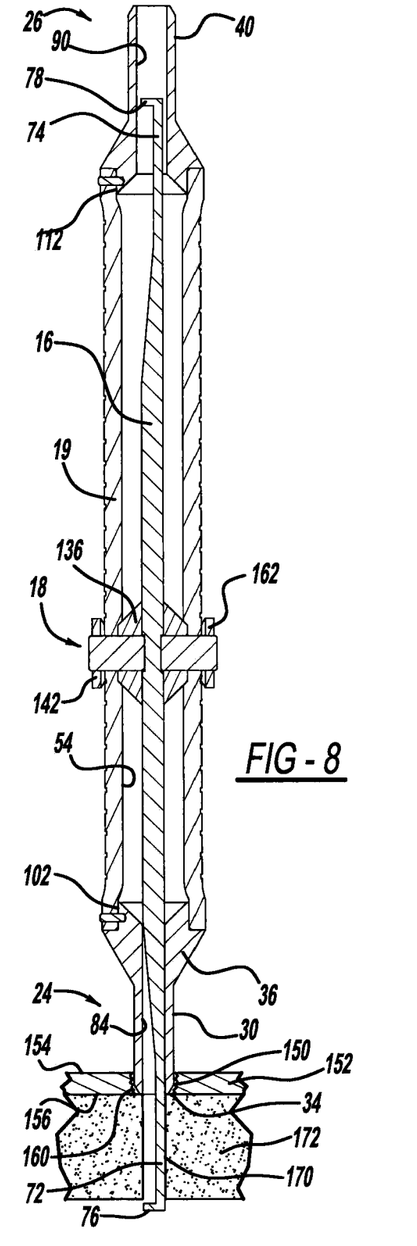
FIG. 8 is a cross-sectional view of the instrument of FIG. 7 and shown with a probe inserted through the bone hole.
Figure 9:
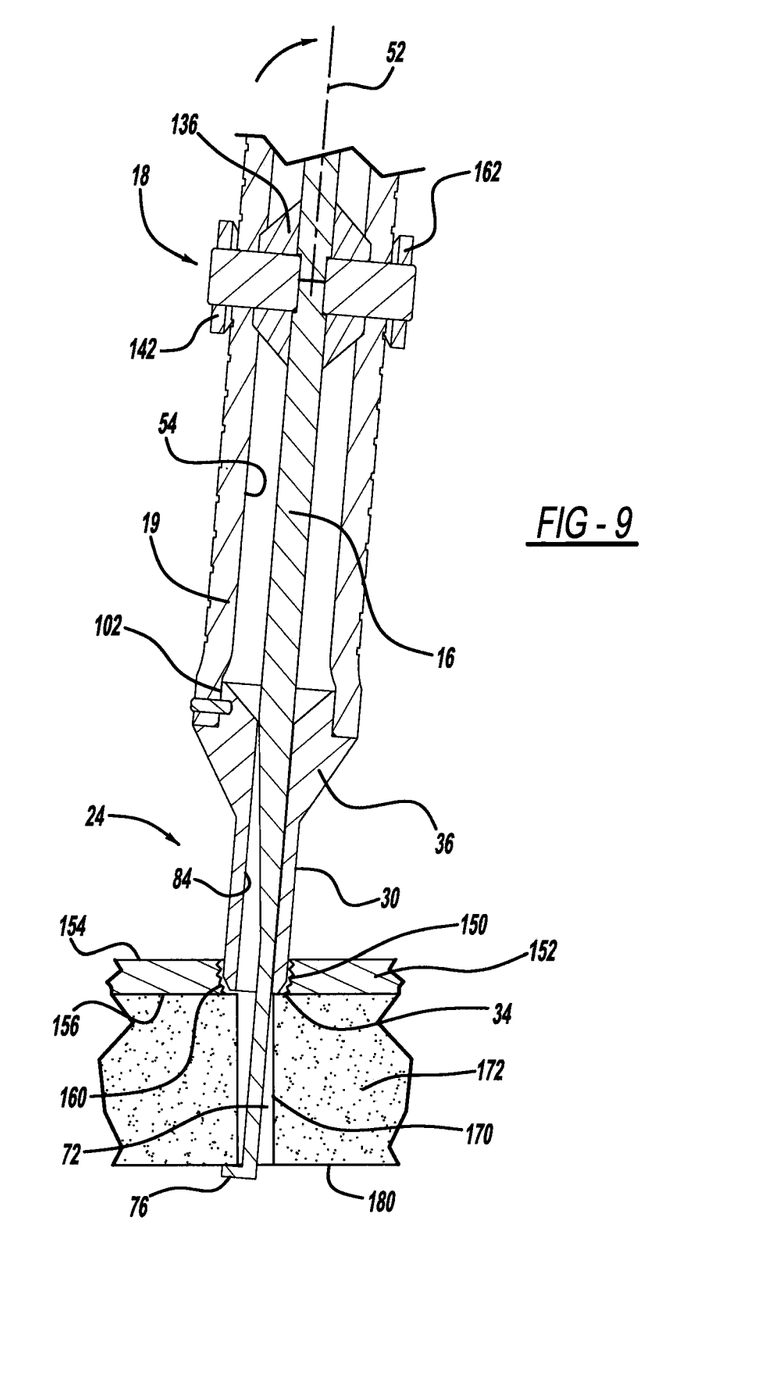
FIG. 9 is a cross-sectional view of the instrument of FIG. 8 and shown with the instrument tilted along its longitudinal axis such that a hook formed on a distal tip of the probe engages an opposite end of the bone where a measurement of the depth of the bone hole can be determined.

With specific reference now to FIGS. 7-9, one example of using the instrument 10 according to the present teachings will be described. Again, it will be appreciated that a surgeon can select the appropriate end of the instrument (the first reference portion 24 or the second reference portion 26) that corresponds with a particular threaded aperture 150 (and corresponding bone screw size) provided in bone plate 152. In the example provided, the aperture 150 includes threads that generally taper from an outer surface 154 to an inner surface 156. Once the proper reference portion has been identified, such as the first reference portion 24 as will be described in this example, a surgeon partially advances the first distal tip 30 into an aperture 150 until the first registering surface 34 of the first reference portion 24 engages threads 160 that define the aperture 150 of the bone plate 152.

Once the first registering surface 34 engages the threads 160 of the bone plate 152, a surgeon can slidably advance the actuator 18 causing the probe 16 to move through the opening 31 and in a direction toward the bone plate 152. Slidably advancing the actuator 18 toward the bone plate 152 causes the first probe portion 72 to be advanced through a prepared bone hole 170 in bone 172. Once the first probe portion 72 has been advanced far enough through the bone hole 170, the surgeon can rotate the instrument 10 along the axis 52 as shown in FIG. 9 until the first hook 76 engages a far surface 180 of the bone 172. In some examples, it may be necessary to partially retract the first probe portion 72 into the inner cavity 54 to create slight tension on the probe 16 between the hook 76 and the actuator 18. At this point, the surgeon can note the indicia 63 of the first series of gradations 62 that the reference line 166 of the actuator 18 is aligned to indicating the measured depth of the bone hole 170. The instrument 10 can then be removed. A correspondingly sized bone screw can be selected and driven into the bone hole 170 (not shown).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument for measuring a depth of a hole in bone, the instrument comprising:
   an instrument body having a cannulated sleeve that extends between a first end and a second end;
   a first reference portion disposed at the first end of the instrument body;
   a second reference portion disposed at the second end of the instrument body; and
   a probe that selectively and alternatively translates in first and second opposite directions through the cannulated sleeve between a first measuring position and a second measuring position, wherein the probe extends outwardly a distance spaced from the first reference portion in the first measuring position and extends outwardly a distance spaced from the second reference portion in the second measuring position.

2. The instrument of claim 1, further comprising an actuator coupled to the probe and configured to slidably advance along the instrument body causing the probe to selectively and alternatively deploy and retract from the respective first and second ends of the instrument body.

3. The instrument of claim 1 wherein the probe includes first and second hooked ends formed at opposite ends thereof.

4. The instrument of claim 1 wherein the first reference portion comprises a first distal tip having a first elongated body that connects the first registering surface and a first conical connecting portion and wherein the second reference portion comprises a second distal tip having a second elongated body that connects the second registering surface and a second conical connecting portion.

5. The instrument of claim 4 wherein the first elongaged body has a first outer diameter and the second elongated body has a second diameter, wherein the first and second diameters are distinct.

6. The instrument of claim 1 wherein the cannulated sleeve defines an elongated slot formed therethrough, wherein the actuator is configured to slidably translate along the elongated slot.

7. The instrument of claim 1 wherein the actuator has a reference line formed thereon and the instrument body has gradations formed thereon, wherein the reference line is configured to operably align with the gradations formed on the instrument body.

8. An instrument for measuring a depth of a hole in bone, the instrument comprising:
   an instrument body having a cannulated sleeve that extends between a first end and a second end;
   a first reference portion disposed at the first end of the instrument body and having a first registering surface that has a first geometry configured to engage a bone plate;
   a second reference portion disposed at the second end of the instrument body and having a second registering surface that has a second geometry configured to engage a bone plate, the second geometry being distinct from the first geometry;
   a first probe portion that slidably extends from the first end of the cannulated sleeve;
   a second probe portion that slidably extends from the second end of the cannulated sleeve; and
   an actuator coupled to the first and second probe and that is configured to slidably advance along the instrument body causing the first and second probe to selectively and alternatively deploy and retract from the respective first and second ends of the instrument body.

9. The instrument of claim 8 wherein the instrument is configured to selectively and alternatively measure a first distance between the first registering surface and the first probe portion and a second distance between the second registering surface and the second probe portion.

10. The instrument of claim 8 wherein the first probe portion has a first hook disposed at a terminal end thereof.

11. The instrument of claim 10 wherein the second probe portion has a second hook disposed at a terminal end thereof.

12. The instrument of claim 8 wherein the first and second probes are monolithically formed as one piece.

13. The instrument of claim 8 wherein the first reference portion comprises a first distal tip having a first elongated body that connects the first registering surface and a first conical connecting portion and wherein the second reference portion comprises a second distal tip having a second elongated body that connects the second registering surface and a second conical connecting portion.

14. The instrument of claim 13 wherein the first and second elongated bodies are coaxial.

15. The instrument of claim 14 wherein the first elongaged body has a first outer diameter and the second elongated body has a second diameter, wherein the first and second diameters are distinct.

16. The instrument of claim 8 wherein the first and second registering surfaces are conical and taper away from each other.

17. The instrument of claim 8 wherein the cannulated sleeve defines an elongated slot formed therethrough, wherein the actuator is configured to slidably translate along the elongated slot.

18. The instrument of claim 17 wherein the actuator comprises a shaft that operably connects a hub disposed within an inner cavity defined by the cannulated sleeve and a button extending outwardly from the elongated slot.

19. The instrument of claim 17 wherein the actuator has a reference line formed thereon and the instrument body has gradations formed thereon, wherein the reference line is configured to operably align with the gradations formed on the instrument body.

20. A method for measuring a depth of a hole in bone, the method comprising:
   positioning a bone plate against the bone;
   preparing a hole through the bone from a first surface to a second surface;
   determining a size of threaded aperture defined through the bone plate;
   positioning one of a first or second end of an instrument relative to the threaded aperture based on the determination, the first end having a first registering surface, the second end having a second registering surface, the first and second registering surfaces having distinct geometries for alternatively registering with different sized threaded apertures of the bone plate;
   deploying a probe with an actuator from the positioned end of the instrument through the threaded aperture to a position through the bone hole;
   positively engaging a hook formed on the probe to the bone at the second surface; and
   referencing gradations on the instrument with a position of the actuator to determine the depth of the hole.

* * * * *